United States Patent
McHale et al.

(10) Patent No.: US 8,265,723 B1
(45) Date of Patent: Sep. 11, 2012

(54) OXIMETER PROBE OFF INDICATOR DEFINING PROBE OFF SPACE

(75) Inventors: Ryan Timothy McHale, Tustin, CA (US); Walter M. Weber, Laguna Hills, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 1280 days.

(21) Appl. No.: 11/871,690

(22) Filed: Oct. 12, 2007

Related U.S. Application Data

(60) Provisional application No. 60/851,448, filed on Oct. 12, 2006.

(51) Int. Cl.
*A61B 5/1455* (2006.01)

(52) U.S. Cl. .......................... 600/310; 600/322; 600/323

(58) Field of Classification Search ................... 600/310, 600/322, 323, 324, 326, 331, 336
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,553,615 A * | 9/1996 | Carim et al. | 600/324 |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |

(Continued)

*Primary Examiner* — Eric Winakur
*Assistant Examiner* — Chu Chuan (JJ) Liu
(74) *Attorney, Agent, or Firm* — Knobbe, Martens, Olson & Bear LLP

(57) ABSTRACT

An embodiment of the present disclosure seeks to select characteristics of incoming intensity data that cause comparisons of selected characteristics to produce defined probe off space having reduced crossover with defined probe on space. Once defined, the present disclosure compares characteristics of incoming intensity data with the now defined probe off space, and in some embodiments, defined probe on space, to determine whether a probe off condition exists. When a processor determines a probe off condition exists, the processor may output or trigger an output signal that audibly and/or visually indicates to a user that the optical sensor should be adjusted for a proper application to a measurement site.

12 Claims, 9 Drawing Sheets

U.S. PATENT DOCUMENTS

| | | | |
|---|---|---|---|
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,846,190 | A * | 12/1998 | Woehrle ............... 600/330 |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,321,100 | B1 | 11/2001 | Parker |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,510,329 | B2 * | 1/2003 | Heckel ............... 600/310 |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,591,123 | B2 * | 7/2003 | Fein et al. ............... 600/323 |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kianl et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,882,874 | B2 * | 4/2005 | Huiku ............... 600/331 |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| 7,280,858 | B2 | 10/2007 | Al-Ali et al. |
| 2006/0129039 | A1 * | 6/2006 | Lindner et al. ............... 600/323 |
| 2006/0211925 | A1 * | 9/2006 | Lamego et al. ............... 600/310 |

* cited by examiner

FIG. 3

Probe On Ratio Range — 302

| Wavelength | 510 | 520 | 530 | 700 | 720 | 800 | 865 |
|---|---|---|---|---|---|---|---|
| Max Ratio | 4.0622 | 4.0185 | 3.5852 | 1.0000 | 1.1529 | 2.0712 | 2.5688 |
| Min Ratio | 1.4435 | 1.2403 | 1.3010 | 1.0000 | 0.8922 | 0.9316 | 0.9893 |

308 — 310

Probe Off Ratio Range — 304

| Wavelength | 510 | 520 | 530 | 700 | 720 | 800 | 865 |
|---|---|---|---|---|---|---|---|
| Max Ratio | 1.0491 | 1.7501 | 1.2234 | 1.0000 | 1.3123 | 1.4723 | 1.1305 |
| Min Ratio | 0.6942 | 0.4748 | 0.6163 | 1.0000 | 0.6699 | 0.6623 | 0.8293 |

306

OXIMETER PROBE OFF INDICATOR DEFINING PROBE OFF SPACE

PRIORITY CLAIM

This present application claims priority benefit under 35 U.S.C. §119(e) from U.S. Provisional Application No. 60/851,448, filed Oct. 12, 2006, entitled "Oximeter Probe Off Indicator Defining Probe Off Space," which is incorporated by reference herein.

CROSS-REFERENCE TO RELATED APPLICATIONS

The present disclosure is related to U.S. Pat. Nos. 6,526, 300, 6,654,624, and the continuation, continuation-in-part, and divisional applications thereof. The foregoing disclosures are incorporated herein by reference and included in the present provisional filing.

BACKGROUND OF THE DISCLOSURE

1. Field of the Disclosure

The present disclosure relates in general to patient monitoring and in particular to oximeter patient monitors capable of indicating probe off conditions.

2. Description of the Related Art

Oximeter systems providing measurements of a monitored patient have become the standard of care in many patient care settings, including surgical, post surgical, neonatal, general ward, home care, physical training, and the like. In general, oximeter systems accept one or more noninvasive signals from an optical sensor or probe capable of emitting light into a tissue site and capable of detecting light attenuated by the tissue site. Accurate determination of the measurements and audio/visual indications is often dependent upon proper application of the optical sensor to the tissue site. In the present disclosure, "probe on" conditions include their ordinary broad meaning known to one of skill in the art, including designating proper application of an optical probe to a measurement site. "Probe off" conditions include their ordinary broad meaning known to one of skill in the art, including designating improper application of an optical probe to a measurement site.

Many oximeters may fail to accurately detect probe off conditions. As stated, this condition occurs when the optical sensor becomes partially or completely dislodged from the patient (measurement site), but continues to detect signals. Probe off errors can be serious because the oximeter may output normal measurements, and audio/visual indications of the monitored parameters when, in fact, the probe is not properly attached to the patient, probe off errors may potentially lead to missed physiological events.

Several solutions to more accurately monitor and detect probe off conditions are disclosed in U.S. Pat. No. 6,654,624, assigned to Masimo Corporation ("Masimo") of Irvine, Calif., and incorporated by reference herein. For example, the '624 patent discloses monitor-based detection of probe off conditions. In particular, an intelligent, rule-based processor uses signal quality measurements to limit the operating region of the oximeter without significant negative impact on low perfusion performance. These signal-quality operating limits are superimposed on a graph of signal strength versus emitter gain to improve probe off detection. In this manner, the oximeter can reject intensity signals that have sufficient signal strength to fall within an operating region, but that are unlikely to be a plethysmograph signal. One signal quality measurement that is used is pulse rate density, which is the percentage of time detected pulses satisfy a physiologically acceptable model. Another signal quality measurement is harmonic energy ratio, which is the percentage of signal energy that occurs at the pulse rate and its harmonics. The operating region of the oximeter is then defined in terms of signal strength versus gain, signal strength versus PR density and energy ratio versus predefined energy ratio limits. Thus, the '624 disclosure seeks to limit the scope of acceptable probe on space, as defined by signal strength versus gain, PR density, and energy ratios, and seeks to designate all non-probe on space as probe off space.

SUMMARY OF THE DISCLOSURE

An embodiment of the present disclosure seeks to select characteristics of incoming intensity data that cause comparisons of the selected characteristics to produce defined probe off space having reduced crossover with defined probe on space. Once defined, the present disclosure compares characteristics of incoming intensity data with the now defined probe off space, and in some embodiments, probe on space, to determine whether a probe off condition exists. When a processor determines a probe off condition exists, the processor may output or trigger an output signal that audibly and/or visually indicates to a user that the optical sensor should be adjusted for a proper application to a measurement site.

In an embodiment, the characteristics include ratio data, such as, for example, data of signals responsive to the intensity signals normalized through division by one of the intensity signals. Such division generates ratio data channels, each indicative of one intensity signal other than the normalizing signal. The ratio data channels can be monitored during clinical or other trials where probe off conditions are known to exist. Moreover, oximeter manufacturers typically monitor ratio data channels during, for example, the clinical trials to relate acquired data to the accurate determination of physiological parameter measurements and/or the audio and visual indications of the same. Thus, probe off trial data can be usable to determine probe off space defined in the context of the acquired ratio data on two or more data channels. Moreover, the clinical trial data can also be usable to determine probe on space defined in the context of the acquired ratio data on one or more of the ratio data channels during valid patient monitoring.

Once the probe off space, and in some embodiments, the probe on space, is defined, ratio data acquired before, periodically during, randomly or pseudo-randomly during patient measurements, combinations of the same, or the like, can be compared against stored probe off and probe on spaces to determine whether a probe off condition exists.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit its scope.

FIG. 3 illustrates exemplary tables of ratio channel data for probe on and probe off conditions, according to an embodiment of the disclosure.

DETAILED DESCRIPTION OF THE PREFERRED EMBODIMENT

To facilitate a further understanding of the disclosure, the remainder of the description describes the disclosure with reference to specific drawings. Moreover, in this application, reference is made to blood parameters. Some references have common shorthand designations. For example, as used herein, HbCO designates carboxyhemoglobin, HbMet designates methemoglobin, HbT designates total hemoglobin, $SpO_2$ designates functional arterial saturation, and $SpaO_2$ designates fractional arterial saturation. Other shorthand designations such as COHb, MetHb, and tHb are also common in the art for these same constituents. These constituents are generally reported in terms of a percentage, often referred to as saturation, relative concentration, concentration, or fractional saturation. Total hemoglobin is generally reported as a concentration in g/dL. The use of the particular shorthand designators presented in this application does not restrict the term to any particular manner in which the designated constituent is reported.

Figure 1:
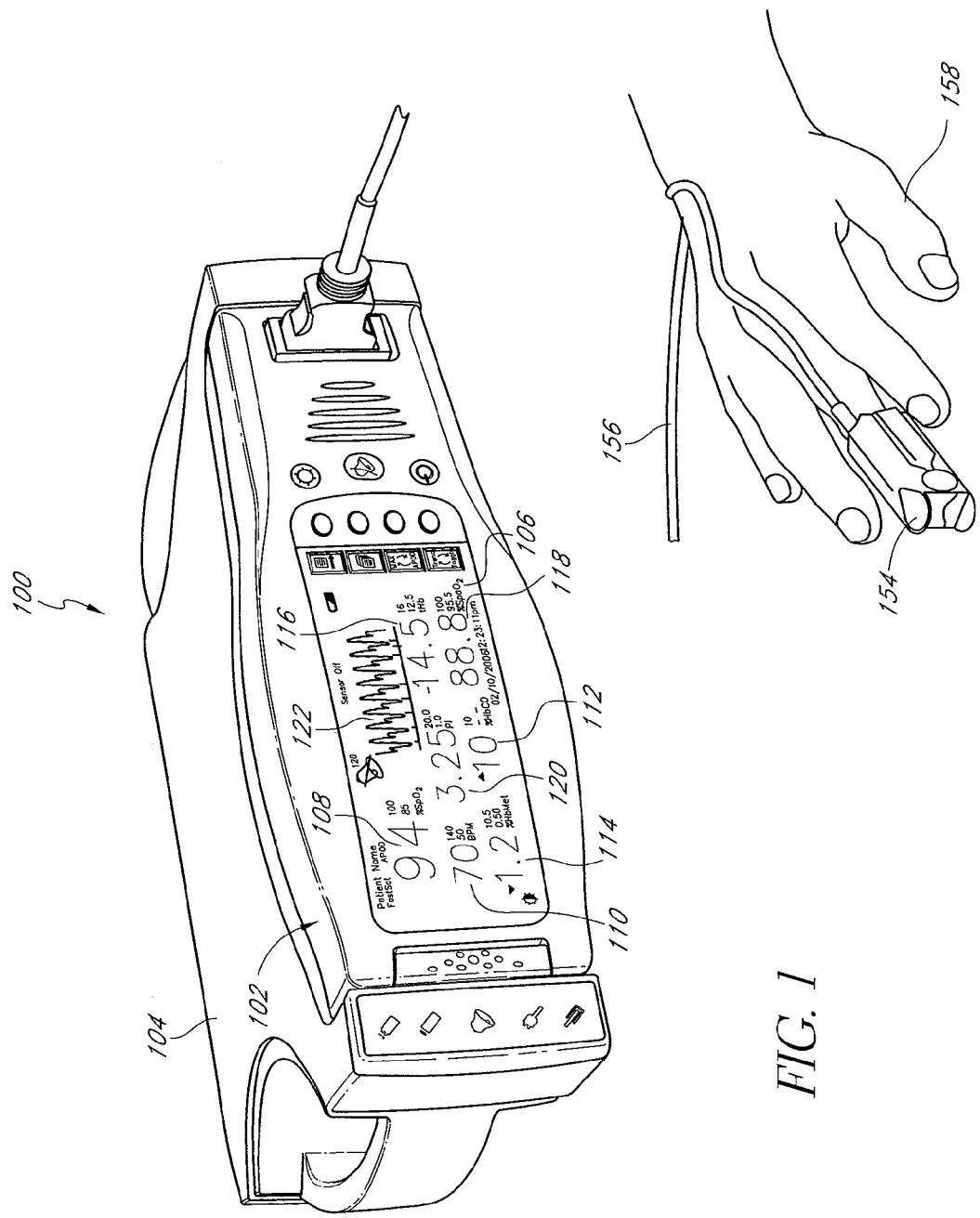
FIG. 1 illustrates an exemplary oximeter patient monitoring system, according to an embodiment of the disclosure.

FIG. 1 illustrates a perspective view of a patient monitor system 100, according to an embodiment of the present disclosure. The system 100 includes a portable patient monitor 102 capable of noninvasively determining one or more physiological parameters. In an embodiment, the portable patient monitor 102 may mechanically and electrically mate with a docking station 104 to recharge batteries, upload and download information, upgrade software or firmware, communicate with other monitors or the like. The monitor 102 also comprises one or more displays 106 capable displaying of a wide variety of measured values in a manner that provides for quick and efficient conveyance of information to a caregiver. For example, the display 106 displays values for HbCO 108, HbMet 109, MbT 110, $SpO_2$ 112, $SpaO_2$ 114, beats-per-minute 116, scaled plethysmograph data 118, PI™ 120 and other information including information audibly and/or visually alerting a caregiver to any probe off conditions. The other information may include historical or trending data, combined parameter data, confidence or perfusion indicators, or the like.

FIG. 1 further illustrates the monitor 102 communicating with a reusable optical sensor 154 through a patient cable 156. In general, the monitor 102 drives the sensor 154 to emit light of differing wavelengths into the body tissue 158. The sensor 154 detects the light after attenuation by the body tissue 158 and outputs a signal indicative of the amount of light received by the sensor 154 through the cable 156. In addition, in some embodiments, the monitor 102 communicates with a temperature sensor and/or a memory device associated with one or more of the sensor 154 and the cable 156.

In an embodiment, the monitor 102 receives sensor output and determines continuous and non-invasive measurements of a wide variety of blood parameters. Although disclosed with reference to the portable monitors 102, an artisan will recognize from the disclosure herein that aspects of the present disclosure can be adopted into tabletop monitors, wireless sensors, or other patient-wearable personal monitors, or multi-parameter patient monitors.

The sensor 154 may advantageously comprise a reusable sensor in the form a clip including a spring biased pivot point capable of removably attaching the reusable sensor to a patient's finger 158. Although disclosed with reference to a reusable sensor having a spring, an artisan will recognize from the disclosure herein that the sensor 154 can advantageously comprise a disposable adhesive type sensor, a combination sensor including reusable and disposable components, components incorporated into other medical devices such as catheters, or the like, or other reusable sensor designs. Moreover, the artisan will recognize from the disclosure herein that the sensor 154 can comprise mechanical structures, adhesive or other tape structures, Velcro wraps or combination structures specialized for the type of patient, type of monitoring, type of monitor, or the like. In an embodiment, the sensor 154 provides data to the monitor 102, and vice versa through the cable 156, although such communication can advantageously be wireless, over public or private networks or computing systems or devices, through intermediate medical or other devices, combinations of the same, or the like. In an embodiment, the monitor 102 may include one or more audio, visual or messaging (pagers, emails, instant and phone messages, vocally presented numbers, messages and alarms, voice-over-IP ("VoIP") interfaces and functionality, or the like) alarms, user input keypad 160, or the like.

Although described in terms of certain embodiments, other embodiments or combination of embodiments will be apparent to those of ordinary skill in the art from the disclosure herein. For example, the monitor 102 may combine other information with intensity-derived information to influence diagnoses or device operation. For example, patterns or changes in the continuous noninvasive monitoring of intensity-derived information may cause the activation of other vital sign measurement devices, such as, for example, blood pressure cuffs. Moreover, the monitor 102 may comprise a personal or wearable noninvasive multi-parameter patient monitor that wirelessly communicates with a monitoring station to provide the monitoring station with measurements for some or all of the physiological parameters measurable by the monitor. For example, the monitor may travel with a patient as the patient, for example, moves through a care site such as a hospital. Wireless networks incorporating such personal pulse technologies are commercially available from Masimo marketed under the brand RadNet™ and RadLink™. Other monitors 102 may include a wireless patient monitor where a traditional sensor communicates with a wireless transmission device wearable, for example, on the wrist. In other embodiments, the wireless transmission device may advantageously be incorporated into a sensor housing adapted for wireless communication. In an embodiment, a wireless receiver communicates with a sensor port in the same manner as a wired sensor. Thus, a traditional sensor and a traditional sensor port may be unaware that a patient cable has been replaced with wireless transmissions.

Figure 2:
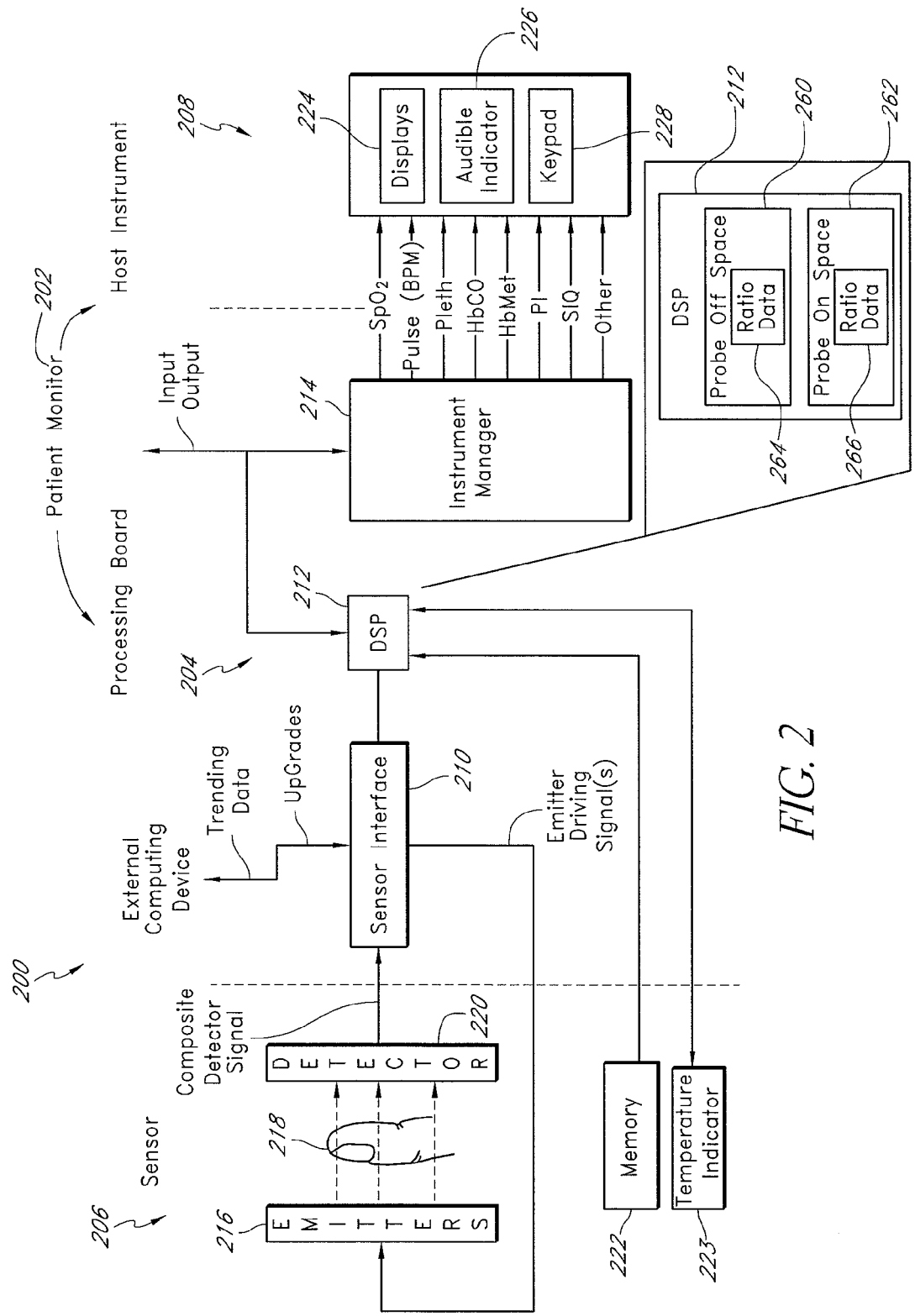
FIG. 2 illustrates an exemplary block diagram of the oximeter patient monitoring system of FIG. 1.

FIG. 2 illustrates an exemplary block diagram of an embodiment of a patient monitoring system 200. As shown in FIG. 2, the system 200 includes a patient monitor 202 comprising a processing board 204 and a host instrument 208. The processing board 204 communicates with a sensor 206 to receive one or more intensity signal(s) indicative of one or more parameters of tissue of a patient. The processing board 204 also communicates with a host instrument 208 to display determined parameter values calculated using the one or more intensity signals. According to an embodiment, the board 204 comprises processing circuitry arranged on one or more printed circuit boards capable of installation into the monitor 202, or capable of being distributed as some or all of one or more OEM components for a wide variety of host instruments monitoring a wide variety of patient information. In an embodiment, the processing board 204 comprises a sensor interface 210, a digital signal processor and signal extractor ("DSP" or "processor") 212, and an instrument manager 214. In general, the sensor interface 210 converts digital control signals into analog drive signals capable of driving sensor emitters, and converts composite analog intensity signal(s) from light sensitive detectors into digital data.

In an embodiment, the sensor interface 210 manages communication with external computing devices. For example, in an embodiment, a multipurpose sensor port (or input/output port) is capable of connecting to the sensor 206 or alternatively connecting to a computing device, such as a personal computer, a PDA, additional monitoring equipment or networks, or the like. When connected to the computing device, the processing board 204 may upload various stored data for, for example, off-line analysis and diagnosis. The stored data may comprise trend data for any one or more of the measured parameter data, plethysmograph waveform data acoustic sound waveform, or the like. Moreover, the processing board 204 may advantageously download from the computing device various upgrades or executable programs, may perform diagnosis on the hardware or software of the monitor 202. In addition, the processing board 204 may advantageously be used to view and examine patient data, including raw data, at or away from a monitoring site, through data uploads/downloads, or network connections, combinations, or the like, such as for customer support purposes including software maintenance, customer technical support, and the like.

According to an embodiment, the DSP 212 comprises a processing device based on the Super Harvard ARChitecture ("SHARC"), such as those commercially available from Analog Devices. However, a skilled artisan will recognize from the disclosure herein that the DSP 212 can comprise a wide variety of data and/or signal processors capable of executing programs for determining physiological parameters from input data. In particular, the DSP 212 includes program instructions capable of receiving multiple channels of data related to one or more intensity signals representative of the absorption (from transmissive or reflective sensor systems) of a plurality of wavelengths of emitted light by body tissue. In an embodiment, the DSP 212 accepts data related to the absorption of two (2) to eight (8) wavelengths of light, although an artisan will recognize from the disclosure herein that the data can be related to the absorption of two (2) to sixteen (16) or more wavelengths.

The processing board 204 also includes the instrument manager 214. According to an embodiment, the instrument manager 214 may comprise one or more microcontrollers controlling system management, including, for example, communications of calculated parameter data and the like to the host instrument 208. The instrument manager 214 may also act as a watchdog circuit by, for example, monitoring the activity of the DSP 212 and resetting it when appropriate.

The sensor 206 may comprise a reusable clip-type sensor, a disposable adhesive-type sensor, a combination sensor having reusable and disposable components, or the like. Moreover, an artisan will recognize from the disclosure herein that the sensor 206 can also comprise mechanical structures, adhesive or other tape structures, Velcro wraps or combination structures specialized for the type of patient, type of monitoring, type of monitor, or the like. In an embodiment, the sensor 206 provides data to the board 204 and vice versa through, for example, a patient cable. An artisan will also recognize from the disclosure herein that such communication can be wireless, over public or private networks or computing systems or devices, or the like.

The sensor 206 includes a plurality of emitters 216 irradiating the body tissue 218 with differing wavelengths of light, and one or more detectors 220 capable of detecting the light after attenuation by the tissue 218. The sensor 206 may also include other electrical components such as, for example, a memory device 222 comprising an EPROM, EEPROM, ROM, RAM, microcontroller, combinations of the same, or the like. In an embodiment, other sensor components may include a temperature determination device 223.

The memory 222 may advantageous store some or all of a wide variety data and information, including, for example, information on the type or operation of the sensor 206; type or identification of sensor buyer or distributor or groups of buyer or distributors, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters for which the sensor is capable of supplying sufficient measurement data (e.g., HbCO, HbMet, HbT, or the like), calibration or parameter coefficient data, software such as scripts, executable code, or the like, sensor electronic elements, whether the sensor is a disposable, reusable, multisite, partially reusable, partially disposable sensor, whether it is an adhesive or non-adhesive sensor, whether the sensor is a reflectance, transmittance, or transreflectance sensor, whether the sensor is a finger, hand, foot, forehead, or ear sensor, whether the sensor is a stereo sensor or a two-headed sensor, sensor life data indicating whether some or all sensor components have expired and should be replaced, encryption information, keys, indexes to keys or hash functions, or the like, monitor or algorithm upgrade instructions or data, some or all of parameter equations, information about the patient, age, sex, medications, and other information that may be useful for the accuracy or alarm settings and sensitivities, trend history, alarm history, or the like. In an embodiment, the monitor may advantageously store data on the memory device, including, for example, measured trending data for any number of parameters for any number of patients, or the like, sensor use or expiration calculations, sensor history, or the like.

The patient monitor 202 also includes the host instrument 208. In an embodiment, the host instrument 208 communicates with the board 204 to receive signals indicative of the physiological parameter information calculated by the DSP 212. The host instrument 208 preferably includes one or more display devices 224 capable of displaying indicia representative of the calculated physiological parameters of the tissue 218 at the measurement site. In an embodiment, the host instrument 208 may advantageously comprise a handheld housing capable of displaying parameter data, including but not limited to pulse rate, plethysmograph data, perfusion quality such as a perfusion quality index ("PI™") signal or measurement quality ("SIQ"), values of blood constituents in body tissue, including for example, $SpO_2$, HbCO, HbMet, Hbt, or the like. In other embodiments, the host instrument 208 is capable of displaying values for one or more of Hbt, Hb, blood glucose, bilirubin, or the like. The host instrument

208 may be capable of storing or displaying historical or trending data related to one or more of the measured values, combinations of the measured values, plethysmograph data, or the like. The host instrument 208 also includes an audio indicator 226 and user input device 228, such as, for example, a keypad, touch screen, pointing device, voice recognition device, or the like.

In still additional embodiments, the host instrument 208 includes audio or visual alarms that alert caregivers that one or more physiological parameters are falling below predetermined safe thresholds. The host instrument 208 may include indications of the confidence a caregiver should have in the displayed data. In a further embodiment, the host instrument 208 may advantageously include circuitry capable of determining the expiration or overuse of components of the sensor 206, including, for example, reusable elements, disposable elements, or combinations of the same.

Although described in terms of certain embodiments, other embodiments or combination of embodiments will be apparent to those of ordinary skill in the art from the disclosure herein. For example, the monitor 202 may comprise one or more monitoring systems monitoring parameters, such as, for example, vital signs, blood pressure, ECG or EKG, respiration, glucose, bilirubin, or the like. Such systems may combine other information with intensity-derived information to influence diagnosis or device operation. Moreover, the monitor 202 may advantageously include an audio system, preferably comprising a high quality audio processor and high quality speakers to provide for voiced alarms, messaging, or the like. In an embodiment, the monitor 202 may advantageously include an audio out jack, conventional audio jacks, headphone jacks, or the like, such that any of the display information disclosed herein may be audiblized for a listener. For example, the monitor 202 may include an audible transducer input (such as a microphone, piezoelectric sensor, or the like) for collecting one or more of heart sounds, lung sounds, trachea sounds, or other body sounds and such sounds may be reproduced through the audio system and output from the monitor 202. Also, wired or wireless communications (such as Bluetooth or WiFi, including IEEE 801.11a, b, or g), mobile communications, combinations of the same, or the like, may be used to transmit the audio output to other audio transducers separate from the monitor 202. In addition, patterns or changes in the continuous noninvasive monitoring of intensity-derived information may cause the activation of other vital sign measurement devices, such as, for example, blood pressure cuffs.

FIG. 2 also illustrates the DSP 112 including memory capable of storing data indicative of a defined probe off space 260 and a defined probe on space 262. In a further embodiment, the spaces 260, 262 include ratio data 264, 266. For example, the probe off space 260 or probe on space 262 may include data acquired through clinical or other trials where data was gathered during known probe off conditions. Examples of such trials may include a myriad of possible common occurrences in hospital or caregiver settings, such as, for example, attaching a reusable clip to a standard hospital bed sheet, instrument pole, clothing, or leaving the clip hanging in the air in one or a variety of lighting conditions. In addition, in an embodiment, the probe off data 260 may include clinical experiments where a sensor hangs approximately eighteen (18) inches off the edge of a desk with a fan set on low placed about three (3) feet from the sensor. Data was collected in five-minute intervals in various lighting conditions, including, for example: (1) ambient light, such as when lights are on in a room; (2) dim or dark light, such as when many of the lights are off in the room; (3) shadow light, such as when lights are off and a separate light is positioned to create shadows from the desk edge that the sensor will swing in to and out of during data collection; (4) reflective light, such as when a box is placed approximately six (6) inches from the sensor with the sensor light emitters facing the box, and (i) all lights are on in the room, and (ii) all other lights are off in the room.

While disclosed with reference to some or all of the foregoing clinical data collections, an artisan will recognize from the disclosure herein that many common probe off environmental conditions could be simulated to create large data sets of ratio channel data during such probe off conditions, including, for example, collection of data when emitters and detector are separated only by air, or the like.

The probe on space 262 may include data acquired through clinical or other trials where data was gathered to, for example, determine correlations between monitor acquired measurement data and clinically or model acquired measurement data. Such experiments carefully monitor the condition of probe placement, and therefore, generally define probe on space. Such probe on space may be further limited using techniques disclosed, for example, in the '624 patent referenced in the foregoing or other techniques recognizable to an artisan from the disclosure herein.

FIG. 3 illustrates exemplary tables 302, 304 of ratio data for probe on 304 and probe off 302 conditions, according to an embodiment of the disclosure. As shown in FIG. 3, the probe off table 302 comprises ratio data ranges for data channels associated with particular wavelengths in at least an eight (8) wavelength oximeter system, the ratio data ranges acquired, for example, during one or more of the foregoing probe off clinical trials. For example, in an embodiment, the monitor drives eight (8) light-emitting diodes (LEDs) with nominal centroids at about 610, about 620, about 630, about 660, about 700, about 730, about 800 and about 905 nm. Although disclosed in reference to certain preferred wavelengths, an embodiment of the eight (8) emission centroids may range from about 605 nm to about 614 nm, from about 615 nm to about 624 nm, from about 625 nm to about 635 nm, from about 655 nm to about 665 nm, from about 690 nm to about 710 nm, from about 720 nm to about 740 nm, from about 785 nm to about 825 nm, and from 875 nm to about 935 nm. An artisan will recognize from the disclosure herein that other wavelengths may be of particular value based on, for example, the absorption spectra of desired physiological parameters, their responsiveness to probe off conditions, or the like. For example, experimental data may determine that wavelengths different from those particularly useful in determining measurement and other displayed data may advantageously be used to determine probe off and/or probe on conditions, as discussed herein. A particular patient monitor may use a certain number of wavelengths for measurement channels and some subgroup or an entirely different additional group of wavelengths for the probe off determinations. For example a monitor may use two (2) to eight (8) or more wavelengths selected for their responsiveness to physiological parameters, and may use one (1) to eight (8) or more overlapping, entirely different, or the like, of wavelengths for probe off and/or probe on determinations. In such embodiments, the wavelengths may be determined based on their ability to clearly distinguish probe off space from probe on space.

Figure 4:
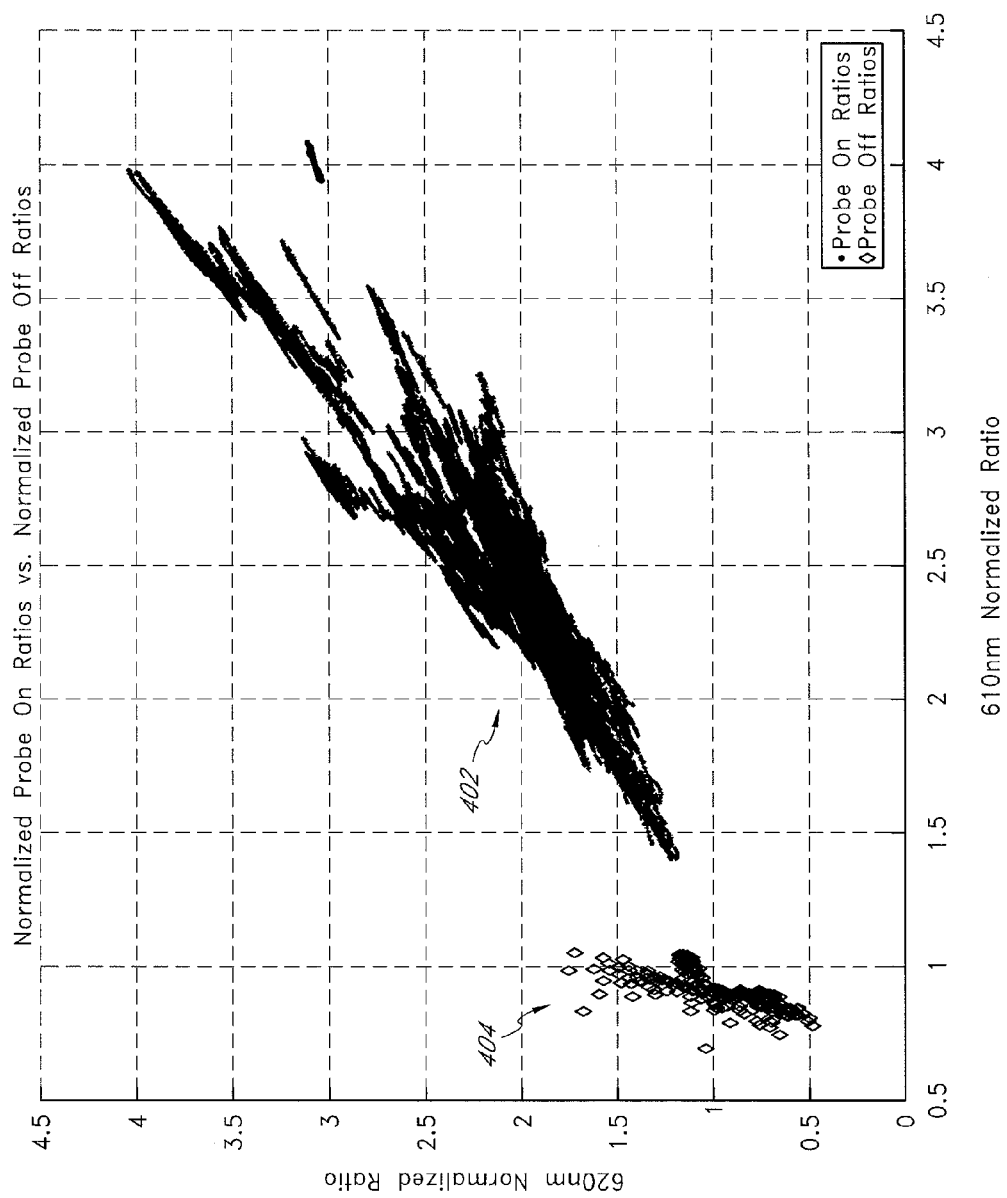
FIGS. 4-7 illustrate exemplary comparative graphs of the ratio channel data of FIG. 3.
Figure 5:
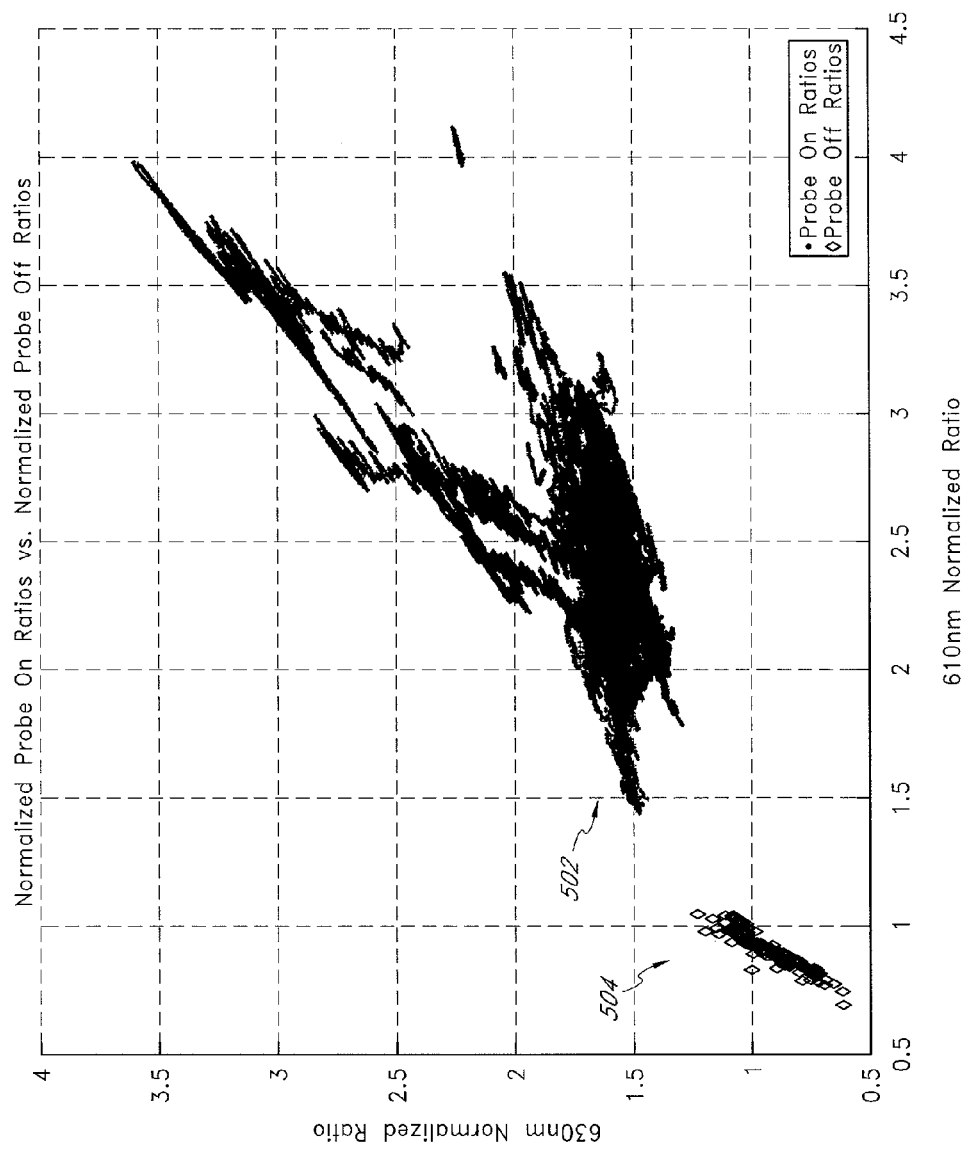
Figure 6:
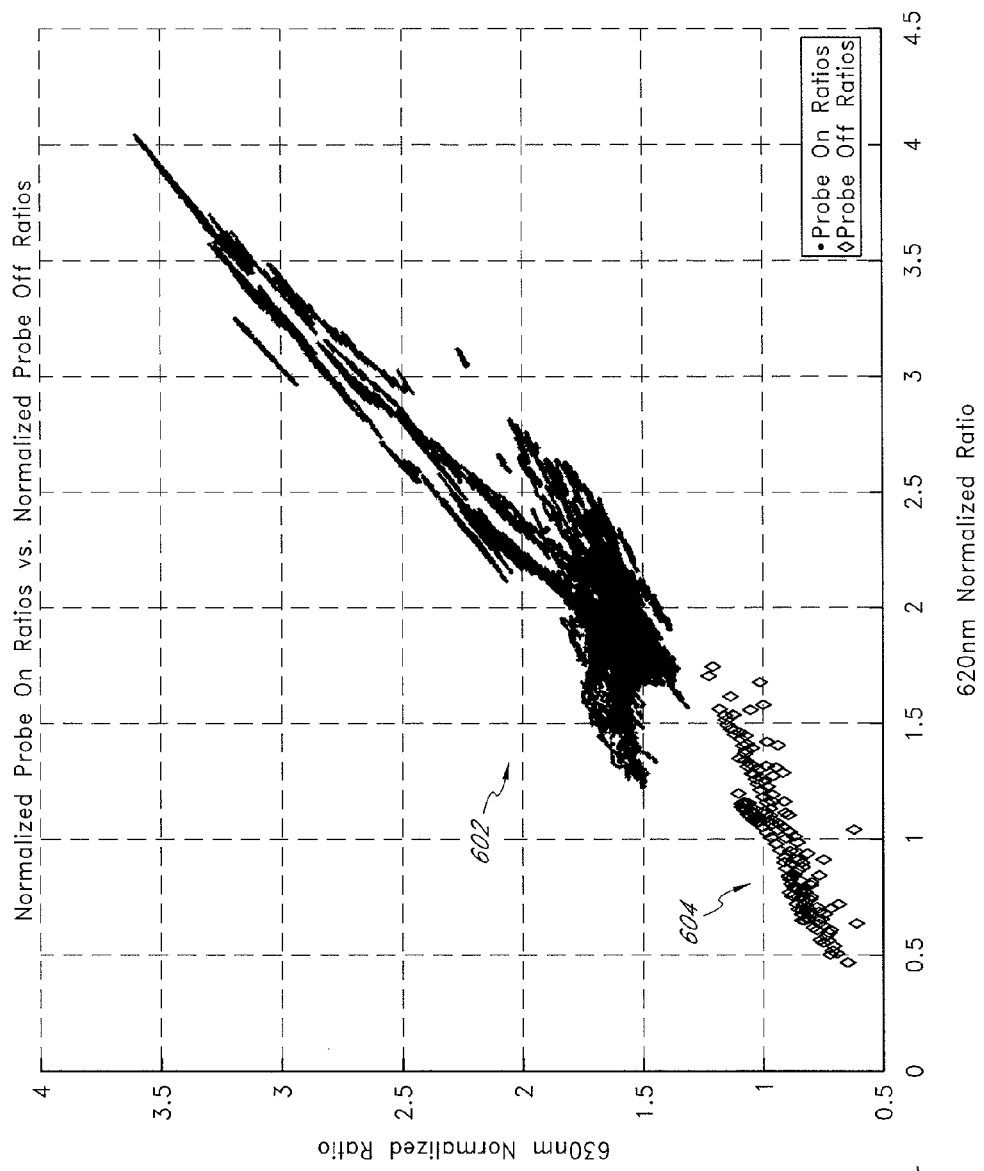

The data channel 306 corresponds to detection of light at approximately 700 nm and is used to normalize the other data channels, although other channels could also be used. From the tables 302, 304, selection of the data channels 308, 310 correspond to light detected from emission of the 610 nm and 630 nm LED's, respectively, increase the likelihood that probe off space can accurately be determined. For example, in the data channels corresponding to the 610 nm and 630 nm LED's the probe off space 302 and the probe on space 304 do not overlap with or otherwise conflict with one another. This distinction can be graphically represented as shown in FIGS. 4-7. For example, FIG. 4 illustrates the distance between valid probe on data or probe on space 402 versus valid probe off data or probe off space 404 for data channels corresponding to the detection of light at 610 and 620 nm. FIG. 5 similarly illustrates the space separation for data channels corresponding to the detection of light at 610 and 630 nm, and FIG. 6 illustrates the space separation for data channels corresponding to the detection of light at 620 and 630 nm. Reviewing FIGS. 4-6 collectively, FIG. 5 shows the clearest or largest distinction between potentially valid probe on space 502 and probe off space 504. Thus, were an oximeter system to made a two (2) dimensional comparison using the foregoing data channels, it would be best served to use the data channels corresponding to the detection of light at 610 and 630 nm.

Figure 7:
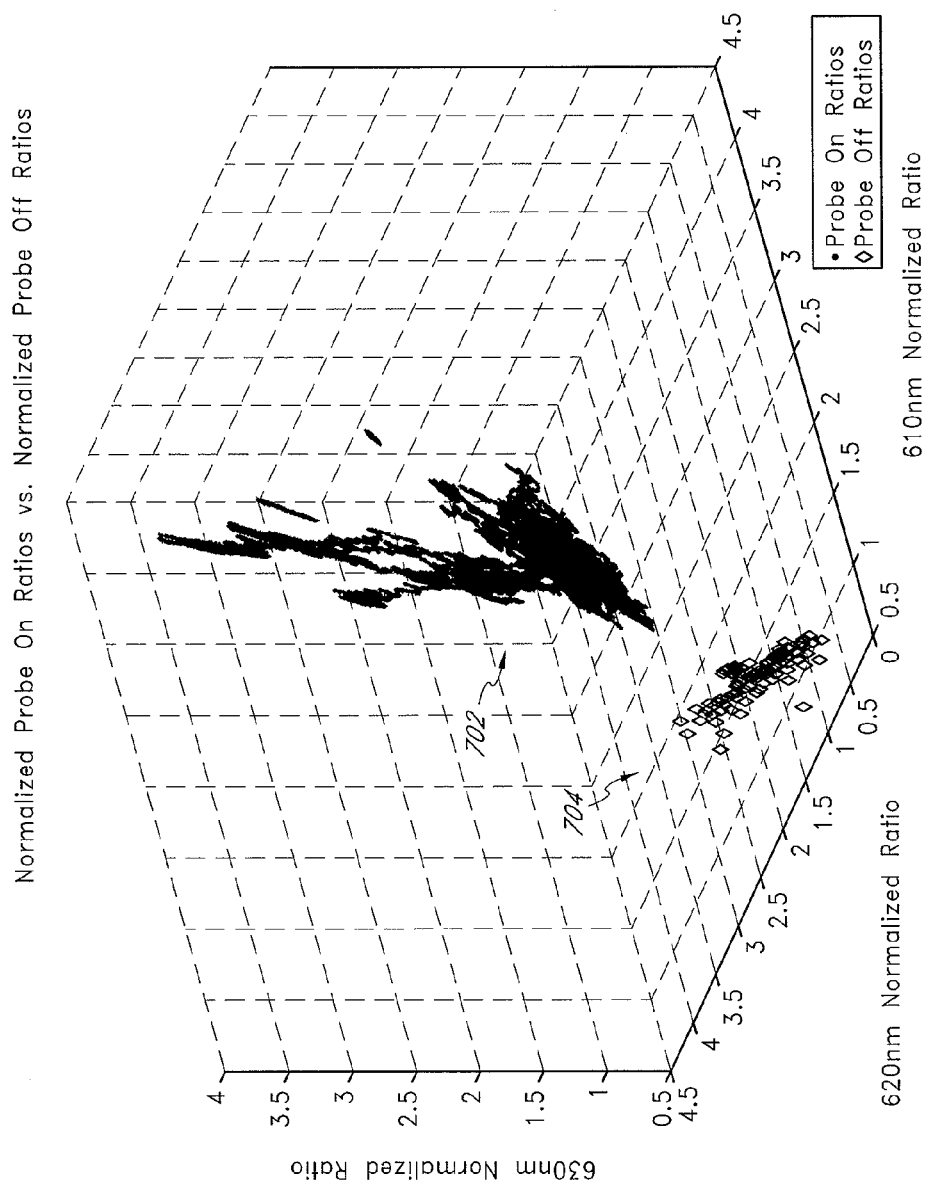

FIG. 7 illustrates a three (3) dimensional graph that combines the data channels corresponding to the detection of light at 610, 620 and 630 nm. Although FIGS. 4 and 6 indicate that the data channel corresponding to 620 nm is not ideal for the separation of spaces, the three (3) dimensional plot of FIG. 7 illustrates that higher dimensions of space increase the separation between defined probe off 704 and probe on 702 regions. Thus, in an oximeter having eight (8) wavelengths of emitted light, a probe off and probe on space may be defined using as many as seven (7) dimensions (the eighth being used for normalization). Such increased dimensional analysis may advantageously provide ever increasing separation between defined probe off and probe on regions.

Figure 8:
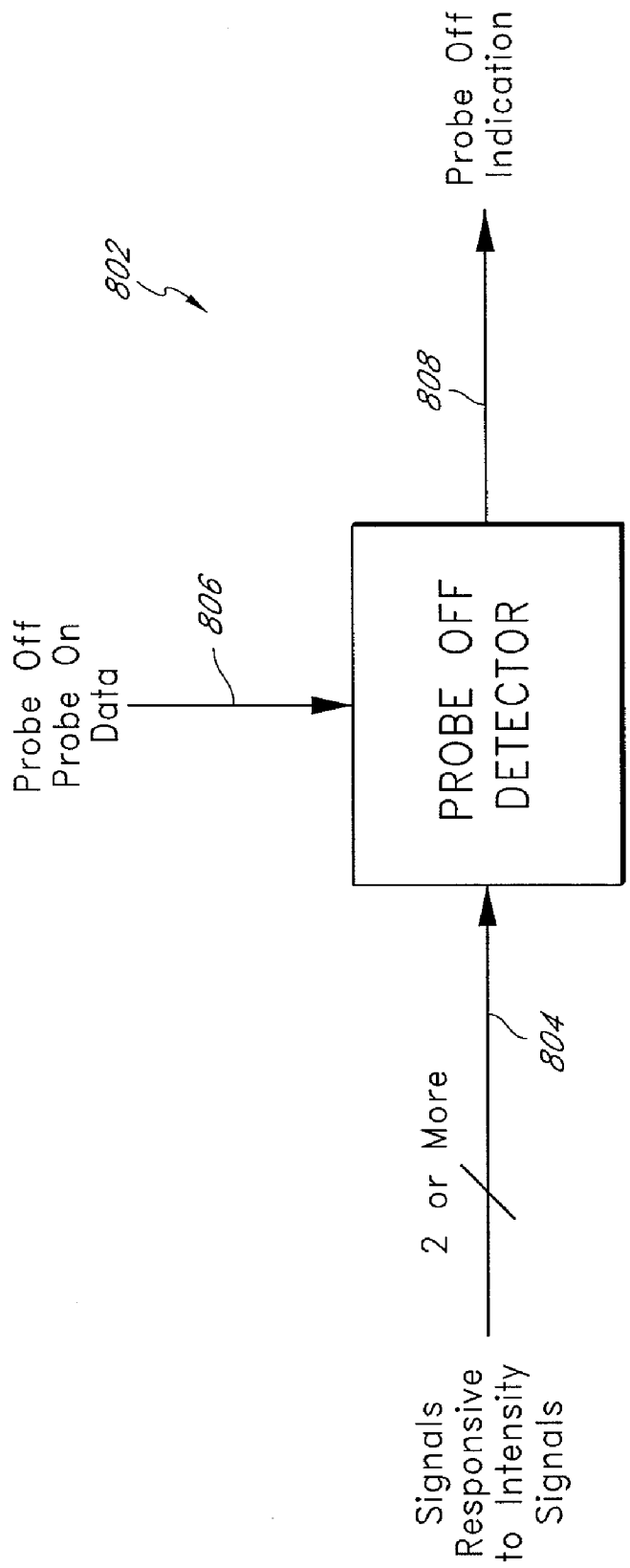
FIG. 8 illustrates a simplified exemplary block diagram of a probe off detector, according to an embodiment of the disclosure.

FIG. 8 illustrates a simplified exemplary block diagram of a probe off detector 802, according to an embodiment of the disclosure. As shown in FIG. 8, the probe off detector 802 includes inputs of data channels 804 corresponding to two (2) or more wavelengths of emitted light, probe off data 806, and in some embodiments, probe on data 806. Comparison of characteristics of the data channels, such as, for example, ratio data, can be compared to multidimensional probe off and/or probe on space to determine and output 808 of a probe off indication.

Figure 9:
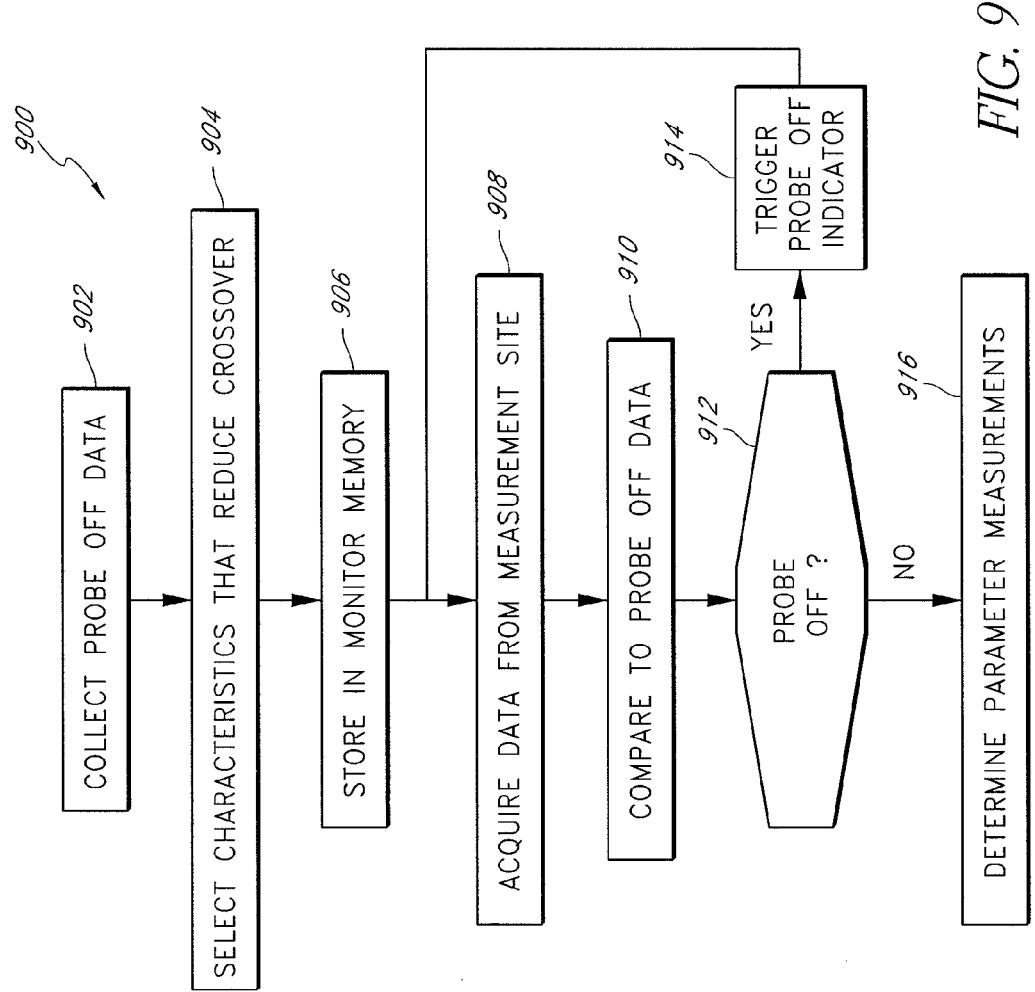
FIG. 9 illustrates an exemplary probe off determination method, according to an embodiment of the disclosure.

FIG. 9 illustrates an exemplary probe off determination process 900, according to an embodiment of the disclosure. The process 900 includes block 902 where probe off data is collected from, for example, clinical trials, mathematical models, extrapolated data, non-probe on data, or the like. In block 904, the collected probe off (and, in some embodiments, probe on data) may be reviewed to determine characteristics that reduce crossover between probe off and probe on space. For example, characteristics may be chosen that decouple the probe off determinations from measurement determinations. For example, when the characteristics comprise ratio data, or normalized data channels responsive to intensity data channels from the sensor, the ratio data corresponding to particular wavelengths may indicate a greater separation between valid parameter data (probe on conditions) and probe off conditions. In some embodiments, increasing the dimensions may advantageously cause further separation between valid and invalid conditions.

In block 906, the probe off data (and in some embodiments, probe on data) is stored in memory on a patient monitor. In an embodiment, such probe on or off data may be updated through upgrading tools, network connectivity such as the internet, smartcards, or other memory devices or network computing. In block 908, the patient monitor acquires data from a measurement site. The acquisition may be at or near a start of data acquisition, periodically throughout acquisition, randomly, in response to particular conditions or changes in conditions, combinations of the same or the like. In block 910, the DSP compares characteristics of the acquired data to the characteristics stored as probe on and off data. Block 912 determines whether a probe off exists by determining whether the characteristics fall within one of the probe off or probe on spaces. When the acquired data falls within the probe off space, a probe off condition is determined to exist and in block 914, the DSP triggers a probe off indicator. The probe off indicator may be an audible sound, such as a constant or varying tone or beep, a visual indicator, such as a flashing and/or colored display or display element(s), combinations of the same or the like. The probe off indicator may comprise help screens or training indicia to guide a caregiver on how to properly attach the probe. The probe off indicator may continue to activate until the probe is properly positioned. In the case of a probe off condition, the process 900 returns to block 908 and acquires data from the measurement site. When a probe off condition does not exist at block 912, block 914 determines parameter measurements according to probe on operation of the patient monitor.

While the probe off indicator has been described in certain embodiments herein, other embodiments of the present disclosure will be known to those of skill in the art from the descriptions herein. Moreover, the described embodiments have been presented by way of example only, and are not intended to limit the scope of the disclosure. Moreover, those of skill in the art understand that information and signals can be represented using a variety of different technologies and techniques. For example, data, instructions, commands, information, signals, bits, symbols, and chips that can be referenced throughout the above description may be represented by voltages, currents, electromagnetic waves, magnetic fields or particles, optical fields or particles, or any combination thereof.

Those of skill in the art further appreciate that the various illustrative logical blocks, modules, circuits, and algorithm steps described in connection with the embodiments disclosed herein can be implemented as electronic hardware, computer software, or combinations of both. To illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or other form of storage medium known in the art. A storage medium is coupled to the processor, such that the processor can read information from, and write information to, the storage medium. In the alternative, the storage medium can be integral to the processor. The processor and the storage medium can reside in an ASIC. The ASIC can reside in a user terminal, physiological monitor and/or sensor. The processor and the storage medium can reside as discrete components in a user terminal, physiological monitor and/or sensor.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Moreover, it is contemplated that various aspects and features of the disclosure described can be practiced separately, combined together, or substituted for one another, and that a variety of combination and subcombinations of the features and aspects can be made and still fall within the scope of the disclosure. Furthermore, the systems described above need not include all of the modules and functions described in the preferred embodiments. Accordingly, the present disclosure is not intended to be limited by the recitation of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A method of determining whether an optical probe in an oximetry system is improperly positioned, the method comprising:
    acquiring data responsive to light attenuated by body tissue;
    comparing characteristics of said data to a probe off space, wherein at least a portion of said probe off space comprises data acquired during known probe off conditions; and
    when said characteristics fall within said probe off space, outputting a probe off indication capable of alerting a caregiver to an improperly positioned probe condition,
    wherein said characteristic comprises normalized data channels corresponding to at least two emitted wavelengths of light, and wherein said at least two emitted wavelengths of light are selected to reduce a likelihood of overlap between said probe off space and probe on space.

2. The method of claim 1, wherein said at least two wavelengths comprise approximately 610 nm and approximately 630 nm.

3. The method of claim 1, comprising comparing characteristics of said data to a probe on space, wherein at least a portion of said probe on space comprises data acquired during known probe on conditions; and when said characteristics fall within said probe on space, determining measurements of monitored physiological parameters.

4. A patient monitor comprising:
    an input receiving data responsive to light attenuated by body tissue, wherein the light comprises light emitted at least two of emission centroids ranging from about 605 nm to about 614 nm, from about 615 nm to about 624 nm, from about 625 nm to about 635 nm, from about 655 nm to about 665 nm, from about 690 nm to about 710 nm, from about 720 nm to about 740 nm, from about 785 nm to about 825 nm, and from 875 nm to about 935 nm;
    a memory storing probe off data corresponding to probe off space, wherein at least some of said probe off space corresponds to data acquired during known probe off conditions; and
    a processor programmed to compare said data received at said input with the probe off data to determine an occurrence of a probe off condition, wherein said comparing includes comparing normalized data channels responsive to said data received at said input, said normalized data channels selected to reduce a likelihood of overlap between said probe off space and probe on space, said processor also programmed to output a probe off indication upon determination of said occurrence.

5. The patient monitor of claim 4, wherein said centroids comprise at least two or more of centroids at about 610, about 620, about 630, about 660, about 700, about 730, about 800 or about 905 nm.

6. The patient monitor of claim 4, wherein said probe off space comprises a multi-dimensional probe off space.

7. The patient monitor of claim 6, wherein said multi-dimensional probe off space includes data responsive to wavelengths of approximately 610 nm and approximately 630 nm.

8. The patient monitor of claim 6, wherein said multi-dimensional probe off space includes data responsive to wavelengths of approximately 610 nm, approximately 620 nm and approximately 630 nm.

9. The patient monitor of claim 4, wherein the memory stores probe on data corresponding to said probe on space, wherein at least some of said probe on space corresponds to data acquired during known probe on conditions; and wherein said processor is programmed to compare incoming data with the probe on data to determine said occurrence of said probe off condition.

10. A patient monitor configured to received signals from a noninvasive optical sensor operatively attached to a patient, to process said signals and determine measurement values for one or more physiological parameters, and to output display indicia responsive to said measurement values to one or more displays, said monitor comprising:
    a sensor interface configured to receive said signals from said noninvasive optical sensor, said signals being responsive to light attenuated by tissue of said patient;
    a processor configured to process said signals to determine a plurality of data channels, each data channel responsive to portions of said signals that represent absorption of a different wavelength of light, said processor also configured to normalize said data channels and to select at least two of said normalized data channels to compare to predetermined data representing a probe off space and a probe on space, said at least two data channels selected to reduce a likelihood of overlap between said data of said probe off space and data of said probe on space, said processor outputting a probe off signal when one or more of said selected data channels sufficiently match said data representing said probe off space; and a caregiver alert configured to activate upon said outputting of said probe off signal to convey to a caregiver that said noninvasive optical sensor is not properly aligned with said tissue of said patient.

11. The patient monitor of claim 10, wherein said at least two normalized data channels are each responsive to absorption by a different one of at least two of wavelengths of light ranging from about 605 nm to about 614 nm, from about 615 nm to about 624 nm, or from about 625 nm to about 635 nm.

12. The patient monitor of claim 11, wherein said wavelengths of light include at least two of about 610 nm, about 620 nm or about 630 nm.

* * * * *